United States Patent [19]

Tranquillini et al.

[11] Patent Number: 5,686,449
[45] Date of Patent: Nov. 11, 1997

[54] 1,5-BENZODIAZEPINES USEFUL AS GASTRINOR CCK-ANTAGONISTS

[75] Inventors: Maria Elvira Tranquillini; Gabriella Finizia; Antonella Ursini, all of Verona, Italy

[73] Assignee: Glaxo Wellcome S.p.A., Verona, Italy

[21] Appl. No.: 532,812

[22] PCT Filed: Apr. 22, 1994

[86] PCT No.: PCT/EP94/01253

§ 371 Date: Oct. 23, 1995

§ 102(e) Date: Oct. 23, 1995

[87] PCT Pub. No.: WO94/25445

PCT Pub. Date: Nov. 10, 1994

[30] Foreign Application Priority Data

Apr. 23, 1994 [GB] United Kingdom .................. 9308421

[51] Int. Cl.⁶ .................... A61K 31/55; C07D 243/12
[52] U.S. Cl. ............................................. 514/221; 540/518
[58] Field of Search ............................... 540/518; 514/221

[56] References Cited

FOREIGN PATENT DOCUMENTS

| | | | |
|---|---|---|---|
| 0 376 849 | 7/1990 | European Pat. Off. | 540/518 |
| 0 514 133 | 11/1992 | European Pat. Off. | 540/508 |
| WO 93 14074 | 7/1993 | WIPO | 540/518 |
| WO 93 14075 | 7/1993 | WIPO | 540/518 |

OTHER PUBLICATIONS

Bock et al., *Journal of Medicinal Chemistry*, vol. 32, No. 1, Jan. 1989, pp. 13–16.

*Primary Examiner*—Robert T. Bond
*Attorney, Agent, or Firm*—Bacon & Thomas

[57] ABSTRACT

The invention relates to compounds of formula (I)

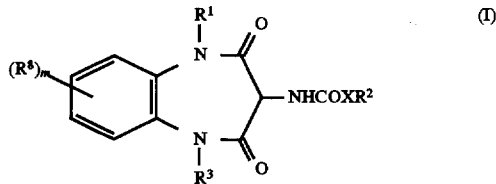

and pharmaceutically acceptable salts thereof having gastrin and/or CCK-B antagonist activity.

15 Claims, No Drawings

1,5-BENZODIAZEPINES USEFUL AS GASTRINOR CCK-ANTAGONISTS

This application is a 371 of PCT/EP94/01,853, filed Apr. 24, 1994 which claims priority of British Application D308421,8 filed Apr. 23, 1993.

This invention relates to novel 1,5-benzodiazepine derivatives, to processes for their preparation, to pharmaceutical compositions containing them and to their use in medicine.

Cholecystokinins (CCK) and gastrin are structurally related peptides which exist in gastrointestinal tissue and in the central nervous system. Cholecystokinins include CCK-33, a neuropeptide of thirty-three amino acids in its originally isolated form, its carboxy terminal octapeptide, CCK-8 (also a naturally-occurring neuropeptide), and 39- and 12-amino acid forms. Gastrin occurs in 34-, 17- and 14-amino acid forms, with the miniumum active sequence being the C-terminal tetrapeptide, Trp-Met-Asp-Phe-NH$_2$ (CCK-4), which is the common structual element shared by both CCK and gastrin.

CCK and gastrin are gastrointestinal hormones and neurotransmitters in the neural and peripheral systems and perform their respective biological roles by binding to particular receptors located at various sites throughout the body.

There are at least two subtypes of cholecystokinin receptors termed CCK-A and CCK-B and both are found in the periphery and in the central nervous system. CCK and gastrin receptor antagonists have been disclosed for preventing and treating CCK-related and/or gastrin related disorders of the gastrointestinal and central nervous systems of animals, and more particularly humans.

U.S. Pat. No. 4,988,692 describes a group of 3-acylamino 1-alkyl-5-phenyl 1,5-benzodiazepine derivatives as cholecystokinin antagonists. Further the specification teaches that the compounds have a significantly greater affinity for the CCK-A receptor over the CCK-B receptor.

We have now found a novel group of 1,5-benzodiazepine compounds which are potent and specific antagonists of gastrin and/or CCK and in particular antagonists of gastrin and/or CCK at the CCK-B receptor.

Thus, the invention provides compounds of general formula (I)

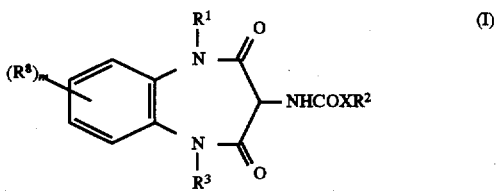

wherein $R^1$ represents a $C_{3-7}$cycloalkyl, $C_{7-11}$ bridgedcycloalkyl or $C_{1-6}$alkyl group which alkyl group may be substituted by a hydroxy, $C_{1-4}$alkoxy, phenyl, $C_{1-6}$alkoxycarbonyl, $C_{3-7}$cycloalkyl, or $C_{7-11}$ bridgedcycloalkyl group;

$R^2$ represents a substituted or unsubstituted phenyl group (wherein the substituents may be 1 or 2 of halo, $C_{1-4}$alkyl, nitro, cyano, trifluoromethyl, trifluoromethoxy, $C_{1-4}$alkylthio or $(CH_2)_n$ $R^4$ wherein $R^4$ is hydroxy, $C_{1-4}$alkoxy, $CO_2R_5$, $NR^5R^6$, $SO_2NR^5COR^7$, $CONR^5SO_2R^7$, or $R^4$ represents a tetrazole, carboxamidotetrazole or 3-trifluoromethyl-1,2-4-triazole group, which groups may be substituted on one of the nitrogen atoms by a $C_{1-4}$alkyl group;

$R^3$ represents $C_{3-7}$cycloalkyl, $C_{7-11}$bridged cycloalkyl or $C_{1-6}$alkyl which alkyl group may be substituted by a phenyl, $C_{3-7}$cycloalkyl or $C_{7-11}$ bridged cycloalkyl group;

$R^5$ represents hydrogen or a $C_{1-4}$alkyl group;

$R^6$ independently represents hydrogen or a $C_{1-4}$alkyl group or the group $SO_2CF_3$;

$R^7$ represents $C_{1-4}$alkyl;

$R^8$ represents hydrogen or a halogen atom; m is zero, 1 or 2;

X represents oxygen or NH;

n is zero or 1; and pharmaceutically acceptable salts and solvates thereof.

It will be appreciated that compounds of formula (I) wherein the groups $R^1$ and $R^3$ are different possess at least one asymmetric carbon atom (namely the carbon atom occupying the 3-position of the diazepine ring) and the invention includes all such stereoisomers and mixtures thereof including the racemates.

In the compounds of formula (I) 'alkyl' when used as a substituent or part of a substituent group means that the group may be straight or branched. Thus, $C_{1-6}$alkyl includes methyl, ethyl, n-propyl, isopropyl, n-butyl, isobutyl or tert-butyl, n-pentyl, isopentyl neopentyl, n-hexyl, isohexyl, 1,3-dimethylbutyl, 3,3-dimethylbutyl, 2,3-dimethylbutyl.

For the groups $R^1$ and $R^3$ the term $C_{3-7}$cycloalkyl as a group or part of a group refers to a monocyclic alkyl group such as cyclopropyl, cylobutyl, cyclopentyl, cyclohexyl or cycloheptyl. The term $C_{7-11}$ bridged cycloalkyl as group or part of a group refers to groups such adamantyl, norbornanyl or norbornenyl.

Halogen in the definition of compounds of formula (I) may represent a fluoro, chloro, bromo or iodo substituent.

When $R^2$ is a phenyl group substituted by a single substituent this may be in the ortho, para or more preferably in the meta position.

When $R^8$ is halogen this is preferably chlorine or fluorine.

When m is 1 or 2 the halogen atom(s) e.g. chlorine or fluorine are preferably in the 7 and/or 8 positions.

When $R^1$ represents an alkyl group substituted by a hydroxyl group this is preferably a $C_{2-6}$alkyl group substituted by hydroxy. Examples of such groups include 2-hydroxyethyl, 3-hydroxypropyl, 2-hydroxypropyl, 2-hydroxy-3-methylbutyl and 2-hydroxy-3,3-dimethylbutyl.

When $R^1$ and/or $R^3$ represents an alkyl group substituted by a $C_{3-7}$cycloalkyl group this may be for example a $C_{2-3}$alkyl group such as ethyl or 1-methylethyl, substituted by a $C_{3-7}$cycloalkyl group such as cyclopéntyl.

When $R^1$ and/or $R^3$ is a bridged $C_{7-11}$cycloalkyl group this may be for example an adamantyl group such as 1-adamantyl or 2-adamantyl group or a 2-norbornanyl group.

When $R^1$ and/or $R^3$ is an alkyl group substituted by a bridged $C_{7-11}$cycloalkyl group this is preferably an ethyl group or more especially a methyl group substituted by a bridged $C_{7-11}$ cycloalkyl group. Examples of suitable bridged cycloalkyl groups include adamantyl such as 1-adamantyl or 2-adamantyl, 2-norbornanyl or 5-norbornenyl.

When $R^1$ is alkyl substituted by phenyl this may be for example benzyl or phenethyl.

When $R^1$ is alkyl substituted by alkoxycarbonyl this is may be for example $C_{1-3}$alkyl such as methyl, ethyl substituted by alkoxycarbonyl such methoxycarbonyl, ethoxycarbonyl or t-butoxycarbonyl.

When $R^4$ represents a tetrazole group suitable examples include

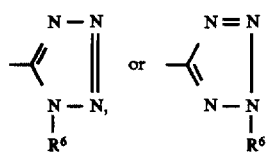

When $R^4$ represents a carboxamidotetrazole grouping suitable examples include

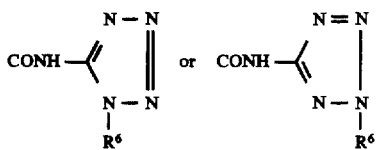

When $R^4$ represents a 3-trifluoromethyl 1,2,4-triazole grouping suitable examples include

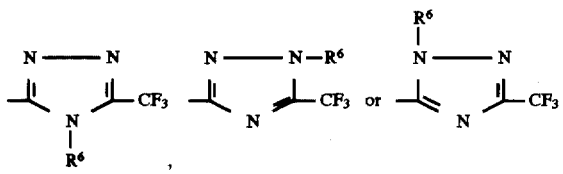

The group $R^6$ has the meanings defined above. It will be appreciated that when $R^6$ represents a hydrogen atom the various isomers for each heterocyclic group are tautomers of that heterocyclic group and all tautomers are included where the formula shows a single tautomer.

Examples of suitable $R^1$ groups include adamantyl, norbornanyl, phenethyl, $C_{1-6}$alkyl e.g. methyl, propyl, isopropyl, butyl, 3-methylbutyl, 3,3-dimethylbutyl, $C_{2-6}$hydroxyalkyl e.g. 2-hydroxyethyl, 3-hydroxypropyl, 2-hydroxpropyl, 2-hydroxy-3-methylbutyl or 2-hydroxy-3,3-dimethylbutyl, $C_{5-7}$cycloalkyl e.g. cyclohexyl, $C_{1-2}$alkyl substituted by a bridged $C_{7-10}$cycloalkyl group e.g. 2-norbornanylmethyl, 5-norbornenylmethyl, 2-adamantylmethyl, 2-adamantylethyl, 2-(1-adamantyl)ethyl, 1-adamantylmethyl, alkoxycarbonylalkyl, e.g. ethoxycarbonylethyl,2-methoxyethyl, or 2-cyclopentylethyl or cyclohexylmethyl.

Examples of suitable $R^3$ groups include $C_{1-6}$alkyl e.g. methyl, 3-methylbutyl, 3,3-dimethylbutyl, $C_{5-7}$cycloalkyl e.g. cyclohexyl, $C_{7-10}$ bridged cycloalkyl e.g. adamantyl or norbornanyl, or $C_{1-2}$alkyl substituted by $C_{5-7}$cycloalkyl, $C_{7-10}$bridged cycloalkyl e.g. 1-adamantylmethyl or cyclohexylmethyl.

Examples of suitable $R^2$ groups include phenyl optionally substituted by bromine, chlorine, fluorine, methyl methoxy, methylthio, trifluoromethyl, cyano, dimethylamino, $CO_2R^5$ wherein $R^5$ is hydrogen or ethyl, $NHSO_2CF_3$, $SO_2NHCOCH_3$, $CONHNSO_2CH_3$,

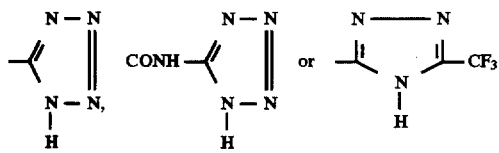

A preferred class of compounds of formula (I) are those wherein the groups $R^1$ and $R^a$ have different meanings.

A further preferred class of compound of formula (I) are those where X is the group NH.

Particularly convenient $R^1$ groups include methyl, propyl, isopropyl, butyl, 3-methylbutyl, 3,3-dimethyl butyl, 2-hydroxyethyl, 3-hydroxypropyl, methoxyethyl, ethoxycarbonylethyl, cyclohexyl or 1-adamantylmethyl.

Particularly convenient $R^3$ groups include 1-adamantyl, 1-adamantylmethyl, cyclohexylmethyl or 3-methylbutyl. More preferably $R^3$ represents 1-adamantyl or 1-adamantylmethyl.

Particularly convenient $R^2$ groups include phenyl or phenyl substituted by methyl, methoxy, dimethylamino, fluoro, $CO_2H$, $CO_2C_2H_5$ or 5-1H-tetrazolyl.

A preferred class of compounds of formula (I) are those wherein $R^1$ represents methyl, 3-methylbutyl, $C_{2-3}$hydroxyalkyl, e.g. 2-hydroxyethyl or 3-hydroxypropyl, 2-ethoxycarbonylethyl, 2-methoxyethyl or cyclohexyl and $R^3$ represents 1-adamantyl or 1-adamantylmethyl.

A further preferred class of compounds are those wherein $R^2$ is phenyl optionally substituted by methyl, methoxy, dimethylamino, fluoro or carboxy.

Compounds of formula (I) wherein $R^8$ represents hydrogen represent yet a further preferred class of compound.

A particularly preferred class of compounds of formula (I) are those wherein $R^1$ represents methyl, 3-methylbutyl, 2-hydroxyethyl, 3-hydroxypropyl, 2-ethoxycarbonylethyl, 2-methoxyethyl or cyclohexyl and $R^3$ represents 1-adamantylmethyl. Within this class especially preferred compounds include those wherein, $R^2$ represents phenyl optionally substituted by methyl, $R^8$ represents hydrogen and X represents NH.

A further particularly preferred class of compounds are those wherein $R^1$ is methyl and $R^3$ is 1-adamantyl. Within this class especailly preferred compounds include those wherein $R^8$ represents hydrogen X represents NH and $R^2$ represents phenyl optionally substutiuted by methyl, fluoro or carboxy.

Particularly preferred compounds:

N-[1-(Adamantylmethyl)-2,4-dioxo-5-(2-hydroxyethyl)-2,3,4,5-tetrahydro-1H-1,5-benzodiazepin-3-yl]-N'-phenylurea;

N-[1-(1-Adamantyl)methyl-2,4-dioxo-5-(2-methoxyethyl)-2,3,4,5-tetrahydro-1H-benzodiazepin-3-yl]-N'-phenylurea;

N-[1-(1-Adamantylmethyl)-2,4-dioxo-5-(3-methylbut-1-yl)-2,3,4,5-tetrahydro-1H-1,5-benzodiazepine-3-yl]-N'-phenylurea.

N-[1-(1-Adamantylmethyl)-2,4-dioxo-5-(cyclohexyl)-2,3,4,5-tetrahydro-1H-1,5-benzodiazepine-3-yl]-N'-phenylurea.

N-[1-Adamantylmethyl)-2,4-dioxo-5-(3-methylbut-1-yl)-2,3,4,5-tetrahydro-1H-1,5-benzodiazepine-3-yl]-N'-[3-(N,N-dimethylamino) phenylurea.

N-[1-Adamantylmethyl)-3-[3(N,N-dimethylamino) phenyloxycarbonyl]amino-2,4-dioxo-5-(3-methylbut-1-yl)-2,3,4,5-tetrahydro-1H-1,5-benzodiazepine.

N-[1-(Adamantylmethyl)-2,4-dioxo-5-(3-hydroxypropyl)-2,3,4,5-tetrahydro-1H-1,5-benzodiazepin-3-yl]-N'-phenylurea;

N-[1-(Adamantylmethyl)-2,4-dioxo-5-(2-ethoxycarbonylethyl)-2,3,4,5-tetrahydro-1H-1,5-benzodiazepin-3-yl]-N'-phenylurea, and enantiomers thereof.

Further particularly preferred compounds include:

1-(1-Adamantan-1-yl-5-methyl-2,4-dioxo-2,3,4,5-tetrahydro-1H-benzo[b][1,4]diazepine-3-yl)-3-m-tolyl-urea;

1-(1-Adamantan-1-yl-5-methyl-2,4-dioxo-2,3,4,5-tetrahydro-1H-benzo[b][1,4]diazepine-3-yl)-3(4-fluoro-phenyl)-urea;

3-[3-(1-Adamantan-1-yl-5-methyl-2,4-dioxo-2,3,4,5-tetrahydro-1H-benzo[b][1,4]diazepine-3-yl)-ureido] benzoic acid; and more especially enantiomers thereof.

The pharmaceutically acceptable salts of the compounds of formula (I) include conventional salts formed for example from pharmaceutically acceptable inorganic or organic acids as well as quaternary ammonium acid addition salts.

Examples of suitable salts include hydrochloric, hydrobromic, sulphuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulphonic, methanesulphonic, naphthalene-2-sulphonic, benzenesulphonic and the like. Other acids such as oxalic, while not in themselves pharmaceutically acceptable, may be useful in the preparation of salts useful as intermediates in obtaining the compounds of the invention and their pharmaceutically acceptable salts.

The compounds of formula (I) in which $R^5$ represents hydrogen may form pharmaceutically acceptable salts with suitable cations. Suitable pharmaceutically acceptable cations include alkali metal (e.g. sodium or potassium) and alkaline earth metal (e.g calcium or magnesium) cations.

References hereinafter to a compound according to the invention includes both compounds of formula (I) and their pharmaceutically acceptable salts and solvates.

The compounds of the invention are potent and specific antagonists of gastrin and/or CCK. The compounds of the invention have been shown to be antagonists of CCK, particularly at CCK-B receptors as demonstrated for example by the compound's ability to inhibit the contractile actions of CCK-4 in the presence of a CCK-A antagonist, in the guinea-pig isolated ileum longitudinal muscle- myenteric plexus.

The compounds of the invention have also been shown to be antagonists of gastrin as demonstrated by their ability to inhibit pentagastrin-stimulated acid secretion from rat isolated gastric mucosa using the procedure described by J. J. Reeves and R. Stables in *Br. J. Pharmac.*, 1985, 86, p.677–684.

Compounds of the invention have also been found to have a significantly weaker activity at CCK-A receptors compared with their activity at gastrin and/or CCK-B receptors, as demonstrated by their ability to inhibit the contractile activity of CCK-8 in guinea-pig isolated ileum longitudinal muscle-myenteric plexus.

The preparation and use of guinea-pig isolated ileum longitudinal muscle-myenteric plexus has been described by K-H Buchheit et al in Nauyn-Schmeideberg's Arch. Pharmacol, (1985), 329, p36–41 and by V. L. Lucaites et al (1991) in J. Pharmacol. Exp. Ther., 256, 695–703.

The greater affinity of the compounds of the invention for the CCK-B receptor over the CCK-A receptor has also been established using the CCK receptor binding assays described by G Dal Forno et al., J. Pharmcol. Exp & Ther. 261, 1056–1063, 1992.

The compounds of the invention are therefore useful for the treatment and/or prevention of disorders in mammals, especially humans, where modification of the effects of gastrin or CCK is of therapeutic benefit. Thus the compounds of the invention are useful for the treatment of central nervous system disorders where CCK and/or gastrin are involved. For example anxiety disorders (including panic disorder, agoraphobia, social phobia, simple phobia, obsessive compulsive disorders, post traumatic stress disorder, and general anxiety disorder), tardive dyskinesia, depression, Parkinson's disease or psychosis. The compounds of the invention are also useful for the treatment of gastrointestinal disorders especially those where there is an advantage in lowering gastric acidity. Such disorders include peptic ulceration, reflux oesophagitis and Zollinger Ellison syndrome. They may also be useful for the treatment of gastrointestinal disorders such as irritable bowel syndrome, excess pancreatic secretion, acute pancreatitis, motility disorders, antral G cell hyperplasia, fundic mucosal hyperplasia or gastrointestinal neoplasms. They may also be useful for the treatment of dependency on drugs or substances of abuse and withdrawal, Gilles de la Tourette syndrome, or dysfunction of appetite regulatory systems; as well as the treatment of certain tumours of the lower oesophagus, stomach, intestines and colon. Compounds of the invention are also useful for directly inducing analgesia, or enhancing opiate or non-opiate mediated analgesia, as well as anaesthesia or loss of the sensation of pain.

The invention therefore provides a compound of formula (I) or a pharmaceutically acceptable salt or solvate thereof for use in therapy, in particular in human medicine.

According to another aspect the invention provides the use of a compound of formula (I) or a pharmaceutically acceptable salt or solvate thereof for the manufacture of a medicament for the treatment of conditions where modification of the effects of gastrin and/or CCK is of therapeutic benefit.

According to a further aspect of the invention we provide a method for the treatment of a mammal, including man, in particular in the treatment of conditions where modification of the effects of gastrin and/or CCK is of therapeutic benefit which method comprises administering an effective amount of a compound of formula (I) or a pharmaceutically acceptable salt or solvate thereof to the patient.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated and the age and the condition of the patient and will be ultimately at the discretion of the attendant physician or veterinarian. In general however doses employed for adult human treatment will typically be in the range of 0.01–2000 mg per day e.g 0.01–500 mg per day.

The desired dose may conveniently be presented in a single dose or as divided doses administered at appropriate intervals, for example as two, three, four or more sub-doses per day.

Because the compounds of the invention antagonise the function of CCK in animals, they may also be used as feed additives to increase the food intake in animals in daily dosages of around 1 mg/kg to 10 mg/kg.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, implant, or rectal administration. Oral administration is preferred.

Tablets and capsules for oral administration may contain conventional excipients such as binding agents, for example, syrup, accacia, gelatin, sorbitol, tragacanth, hydroxypropyl cellulose, mucilage of starch or polyvinylpyrrolidone; fillers, for example, lactose, sugar, microcrystalline cellulose, maize-starch, calcium phosphate or sorbitol; lubricants, for example, hydrogenated vegetable oils, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in prefilled syringes, vials and ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form which may be obtained by freeze drying for constitution with a suitable vehicle, e.g. sterile, pyrogen-free water, before use.

The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

Compounds of general formula (I) may be prepared by reacting the amine (11) wherein $R^1$, $R^3$ $R^8$ and m are as defined in formula (I).

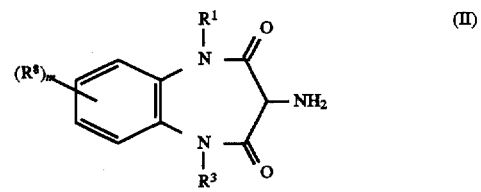

or with an isocyanate $R^2NCO$, or a compound $R^2XCOCl$ wherein $R^2$ and X have the meaning defined above.

The reaction conveniently takes place in the presence of a suitable solvent such as a halohydrocarbon (e.g. dichloromethane), an ether (e.g tetrahydrofuran) or a nitrile (e.g. acetonitrile) or a mixture thereof at a temperature in the range of 0° C. to 80° C.

Compounds of formula (II) may be prepared by reduction of compounds of formula (III)

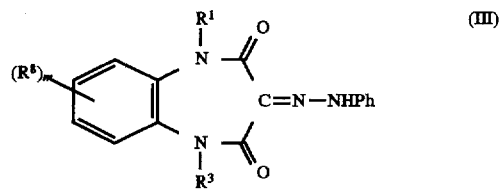

The reduction may be carried out using zinc and acetic acid and at a temperature within the range of 0°–50°. Alternatively the reduction may be carried out using ammonium formate and palladium on charcoal in a solvent such as methanol.

Compounds of formula (III) may be prepared by reaction of the orthophenylenediamine (IV) with the diacid chloride (V), in a suitable solvent such as an ether e.g. tetrahydrofuran or ethyl acetate

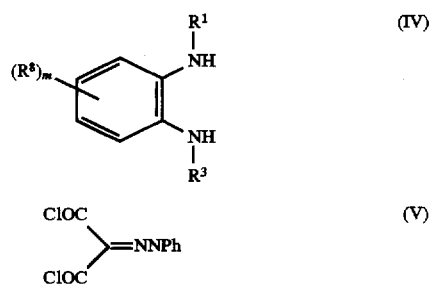

Compounds of formula (IV) are either known compounds or may be prepared by analogous methods. Thus for example a compound of formula (IV) may be prepared by alkylation of the amine (VI).

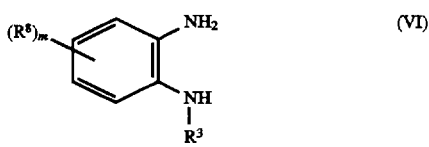

Thus the amine (VI) may be reacted with the compound $R^1Y$, in which Y is chlorine or bromine, optionally in the presence of sodium iodide in a solvent such as N,N-dimethylformamide.

Compounds of formula (IV) where in $R^1$ is an optionally substituted alkyl group. may also be prepared from compound (VI) by reaction with a suitable aldehyde or ketone with concomitant or subsequent reduction of the reaction product.

Compounds of formula (I) wherein $R^1$ or $R^3$ is an optionally substituted alkyl group may be prepared by alkylation of a compound corresponding to that of formula (I) but wherein $R^1$ or $R^3$ represents hydrogen. The alkylation process may be carried out using an appropriate compound $R^1Y$ or $R^3Y$ wherein Y is a leaving group e.g. bromine in the presence of a suitable base and in an aprotic solvent. Thus for example the reaction may be carried out using sodium hydride as the base in a solvent such as N,N-dimethylformamide. Alternatively the reaction may be carried out in a solvent such as a ketone e.g. acetone and in the presence of an alkali metal carbonate e.g. sodium or potassium carbonate.

Compounds of formula (I) may also be converted into other compounds of the invention.

Thus compounds of formula (I) wherein $R^2$ is a phenyl group substituted by a carboxyl group may be prepared by hydrolysis of the corresponding compound of formula (I) wherein $R^2$ is a phenyl group substituted by an alkoxycarbonyl group.

Compounds of formula (I) wherein $R^1$ represents a $C_{2-6}$hydroxyalkyl group may be prepared by reduction of the corresponding compound wherein $R^1$ represents an alkoxycarbonyl $C_{1-5}$alkyl group.

In the processes described above the groups $R^1$ and $R^3$ in the intermediates II, III, V and VI may be a group as defined in formula (I) or a group convertible thereto.

Compounds of formula (I) contain at least one asymmetric carbon atom, namely the carbon atom of the diazepine ring to which the substituted urea grouping is attached. Specific enantiomers of the compounds of formula (I) may be obtained by resolution of the racemic compound using conventional procedures such as chiral HPLC. Alternatively the required enantiomer may be prepared by the corresponding enantiomeric amine of formula (II) using any of the processes described above for preparing compounds of formula (I) from the amine (II).

The enantiomers of the amine (II) may be prepared from the racemic amine (II) using conventional procedures such as salt formation with a suitably optically active acid such as R- camphorsulphonic acid. Alternatively the racemic amine may be alkylated on the amino group to introduce a suitable enantiomeric benzyl group e.g. reaction with (S)-(+)-2-(4-toluenesulphonyloxy)-phenylacetic acid methyl ester. The resultant mixture of diastereoisomers may then be separated by conventional means e.g. chromatography and then the amino protecting group removed by catalytic hydrogenolysis e.g. palladium using for example palladium hydroxide on charcoal and hydrogen in a suitable solvent e.g. methanol.

The following examples, which are non-limiting, illustrate the invention. In the Preparations and Examples, unless otherwise stated: Melting points (m.p.) were determined on a Buchi m.p. apparatus and are uncorrected. All temperatures refer to 0C. Infrared spectra were measured in chloroform-$d_1$ solutions on a FT-IR instrument. Proton Magnetic Resonance (1H-NMR) spectra were recorded at 300MHz as solutions in chloroform-$d_1$. Chemical shifts are reported in ppm downfield (d) from Me4Si as an interna l standard, and are assigned as singlets (s), doublets (d), doublet of doublets (dd) or multiplets (m). Column chromatography was carried out over silica gel (Merck AG Darmstadt, Germany). Solutions were dried over anhydrous sodium sulphate. "Petrol" refers to petroleum ether, b.p. 40°–60° C. Dichloromethane was redistilled over calcium hydride; tetrahydrofuran was redistilled over sodium; ethyl ether was redistilled over sodium and ethyl acetate was dried over activated molecular sieves. The following abbreviations are used in the text. EA=ethyl acetate, CH=cyclohexane, P=petroleum ether 40°–60° C, THF=tetrahydrofuran, DCM=dichloromethane, EE=ethyl ether, DMF=N,N-dimethylformamide. Tlc refers to thin layer chromatography on silica plates.

INTERMEDIATE 1

N-(1-Adamantylmethyl)-1,2-phenylenediamine 1,2-Phenylenediamine (5 g) was added to a solution of 1-adamantanecarboxaldehyde (7.6 g) in methanol (100 ml). The solution was stirred at 23° for 2 h, then sodium borohydride (3.5 g) was added portionwise. The resulting mixture was stirred at 230 for 2 h, then diluted with ethyl acetate (400 ml) and filtered. The organic layer was washed with brine (300 ml), dried and concentrated in vacuo to a residue, which was taken up in ethyl ether and the inorganic salts still present were removed by filtration. The filtrate was concentrated in vacuo and purified by flash chromatography to give the title compound as a beige solid (1.2 g). M.p.86°–7° T.l.c. CH-EA (7:3), Rf 0.6.

INTERMEDIATE 2

N-(1-Adamantylmethyl)-N'-(3-methylbut-1-yl)-1,2-phenylenediamine

Bromo 3-methylbutane (0.43 ml) was added to a solution of intermediate 1 (1.0 g) and sodium iodide (0.58 g) in DMF (50 ml) under a nitrogen atmosphere. The resulting solution was heated to 130C for 5 h. The solution was allowed to cool to room temperature, diluted with water (100 ml) and extracted with diethyl ether (2×100 ml). The combined organic extracts were washed with brine (150 ml), dried and concentrated in vacuo to an oil which was purified by flash chromatography (eluting with CH-EA 95:5) to give the title compound as a beige solid (0.7 g). M.p.64°–5° T.l.c. CH-EA (9:I ), Rf 0.82.

INTERMEDIATE 3

1-(1-Adamantylmethyl)-2,4-dioxo-5-(3-methylbut-1-yl)-3-phenylhydrazono-2,3,4,5-tetrahydro-1H-1,5-benzodiazepine The intermediate 2 (0.7 g) and 2-phenylhydrazonomalonyldichloride (0.63 g) were each taken up in tetrahydrofuran (20 ml) and dropped in a flask containing tetrahydrofuran (10 ml) under a nitrogen atmosphere. After complete addition the solution was heated to 50° for 1 h. The solution was concentrated in vacuo to an oil which was purified by flash chromatography (eluting with CH-EA 9:1) to give the title compound as a yellow solid (0.66 g). M.p.104–5C T.l.c. CH-EA (7:3), Rf 0.68.

INTERMEDIATE 4

1-(1-Adamantylmethyl)-3-amino-2,4-dioxo-5-(3-methylbut-1-yl)-2,3,4,5-tetrahydro-1H-1,5-benzodiazepine Zinc dust (0.59 g) was added to a solution of the intermediate 3 (0.63 g) in glacial acetic acid (3 ml). The mixture was stirred at 23° for 4 h, then decanted from zinc. The solution was basified until pH=9 using 10% sodium hydroxide solution and extracted with ethyl acetate (2×50 ml). The combined organic extracts were washed with brine (50 ml), dried and concentrated in vacuo to a residue which was triturated with diethyl ether to give the title compound as a white solid (0.36 g). M.p. 218°–9°. T.l.c. EA-MeOH (95:5), Rf 0.32. IR :3352 and 3400 (NH2), 1686 and 1659 (C=O), 1597 (C=C) cm-1; 1H-NMR : 7.44–7.37 (m); 7.36–7.26 (m); 4.42 (d); 4.01 (s); 3.93 (m); 3.25 (d); 2.12 (m); 1.84 (m); 1.8–1.2 (m); 0.95 (d).

INTERMEDIATE 5

2-Nitro-N-cyclohexyl aniline

Cyclohexylamine (8.1 ml) was added dropwise to 1-fluoro-2-nitrobenzene (4) (3.7 mg) under a nitrogen atmosphere at 0°. To the resulting orange solid, dry toluene (10 ml) was added and the mixture was stirred at 23 ° C. for 30 min. then diluted with dichloromethane/methanol 1/1 (100 ml) and the organic layer was washed with brine (50 ml), 10 % solution sodium hydroxide (50 ml) and brine (50 ml), dried and concentrated in vacuo to give the title compound as an orange solid (7.45 g). Mp 105°–7° T.l.c. CH-EA (7:3). Rf 0.78

INTERMEDIATE 6

2-Amino-N-cyclohexyl aniline

Potassium carbonate (29.9 g) and Sodium hydrosulphite (26.3 g) were added portionwise to a suspension of intermediate 5 (7.33 g) in ethanol/water 1/1 (400 ml) under stirring. After 2 h a further amount of potassium carbonate (30.8 g) and sodium hgydrosulphite (28.2 g) were added and the resulting suspension was stirred at 23° C. for 20 h., then acidified to pH=3.5 with conc.hydrochloric acid and concentrated in vacuo. A 10% solution of sodium hydroxide was added until pH=10 and the solution was extracted with dichloromethane (2×150 ml). The combined organic extracts were washed with brine (150 ml), dried and concentrated in vacuo to the crude compound (5.27 g) which was purified by flash chromatography (eluting with CH-EA 90:10 )to give the title cmpound as a red-brown oil (2.81 g). T.l.c. CH-EA(1/1), Rf 0.65. IR: 3389-3373 (NH+NH2) ;1601 (C=C) cm-1;

INTERMEDIATE 7

N-(1-Adamantylmethyl)-N'-)cyclohexyl)-1,2-phenylenediamine

To a solution of intermediate 6 (2.69 g) in methanol (100 ml), 1-adamantanecarboxaldehyde (2.34 g) in methanol (50 ml) was added. The solution was stirred at 230 for 30 min, then sodium borohydride (4.80 g) was added portionwise. The resulting mixture was stirred at 23C for 2 h, then diluted with ethyl acetate (200 ml), the organic layer was washed with 10% solution potassium carbonate (2×100 ml ), brine (2×100 ml), dried and concentrated in vacuo to a residue which was purified by flash chromatography (eluting with CH-EA 24/1 ) to give the title compound as a purple oil (1.79 g). T.l.c. CH-EA (19/1), Rf 0.65.

INTERMEDIATE 8

1-(1-Adamantylmethyl)-2,4-dioxo-5-(cyclohexyl)-3-phenylhydrazono-2,3,4,5-tetrahydro-1H-1,5-benzodiazepine The intermediate 7 (1.72 g) and the 2-phenylhydrazonomalonyldichloride (1.50 g) were each taken up in THF (25 ml) and dropped in a flask containing THF (10 ml) under a nitrogen atmosphere. After complete addition the solution was stirred at 20° for 2 h then heated at 70° for 2 h; it was diluted with ethyl acetate (100 ml), the organic layer was washed with 10% solution sodium hydrogen carbonate (100 ml ), brine (100 ml), dried and concentrated in vacuo to a residue (2.6 g) which was purified by flash chromatography (eluting with CH-EA 8/2) to give the title compound as a yellow foam (2.29 g) T.l.c. CH-EA (8/2), Rf 0.51.

INTERMEDIATE 9

1-(1-Adamantylmethyl)-3-amino-2,4-dioxo-5-(cyclohexyl)-2,3,4,5-tetrahydro-1H-1,5-benzodiazepine Zinc dust (2.93 g) was added portionwise to a solution of the intermediate 8 (2.19 g) in glacial acetic acid (70 ml). The mixture was stirred at 23° for 2 h, then a further amount of Zinc was added (1 g ) and stirring was continued for 20 h. Zinc was filtered off through a pad of celite, the filtrate was evaporated and the residue was taken up in etheyl acetate (200 ml ) washed with 10% sodium hydroxide solution and brine (100 ml), dried and concentrated in vacuo to a residue (1.93 g) which was purified by flash chromatography (eluting with EA/MeOH 95/5 to give the title compound (1.28 g). T.l.c. EA-MeOH. (9/1) Rf 0.56.

INTERMEDIATE 10

N-Adamantan-1-yl-2-nitro-phenylamine

A mixture of 2-chloronitrobenzene (10 g), potassium carbonate (17.5 g) copper (I) iodide (609 mg) and 1-adamantanamine (19.2 g) was heated at 180° under nitrogen for 6 h. The mixture was allowed to cool to room temperature and was adsorbed onto silica. This was chromatographed with hexane-EA (9:1) as eluent to give the title compound (10.86 g) as an orange/brown crystalline solid containing 29% 2-chloronitrobenzene. T.l.c. (99:1 hexane-EA) Rf 0.23

INTERMEDIATE 11

N-Adamantan-1-yl-benzene-1,2-diamine

A solution of N-Adamantan-1-yl-2-nitro-phenylamine (6 g) prepared as in intermediate 10 in ethyl acetate (120 ml) was hydrogenated at 23° and 1 atm. pressure over 5% platinum on carbon (600 mg) for 2 h. The catalyst was removed by filtration through hyflo and the filtrate evaporated to give a brown solid. This was adsorbed onto silica and chromatographed with hexane-EA (20:3) as eluent to give the title compound (3.45 g) as cream crystals, m.p. −69°–71°.

INTERMEDIATE 12

N-Adamantan-1-yl-N'-methyl-benzene1,2-diamine

Methyl iodide (0.564 ml) was added to a mixture of intermediate 11 (2 g) and potassium carbonate (1.75 g) in dry DMF (8 ml) at 23° under nitrogen. After 4.5 h, the mixture was poured into water (100 ml) and extracted with EA (2×100 ml). The combined extracts were washed with water and saturated brine then dried and evaporated. The residue was chromatographed with hexane- EA (8:1 to 6:1 to 4:1) as eluent to give a 70:30 mixture of the title compound with N-adamantan-1-yl-N-methylbenzene-1,2-diamine (904 mg) as a yellow solid, m.p. 68°–76° dec.

INTERMEDIATE 13

1-Adamantan-1-yl-5-methyl-3-)phenyl-hydrazono)-1,5-dihydro-benzo[b][1,4]diazepine-2,4-dione Solutions of intermediate 12 used without purification (878 mg) and 2-(phenyl-hydrazono)-propanedioyl dichloride (841 mg) in dry THF (30 ml) were added simultaneously and dropwise over 25 min to dry THF (30 ml) at −5° under nitrogen. After 24 h the solution was evaporated to dryness and the residue partitioned between 1N $Na_2CO_3$ solution (150 ml) and EA (2×100 ml). The combined organic phases were washed with saturated brine, dried and evaporated. The residue was chromatographed on $Et_3N$ deactivated silica with hexane-EA (2:1) as eluent to give the title compound (551 mg) as a crunchy yellow foam.

T.l.c. $Et_3N$ deactivated $SiO_2$ (1:1 hexane-EA) Rf 0.28

13

I.r. (Solution in CHCl₃)2912;1651;1520;1377;1189; 820cm⁻¹

INTERMEDIATE 14

1-Adamantan-1-yl-3-amino-5-methyl-1,5-dihydro-benzo[b][1.4]diazepine-2.4-dione

A solution of intermediate 13 (530 mg) in glacial acetic acid (6 ml) was added dropwise to a suspension of zinc dust (568 mg) in glacial acetic acid (4 ml) in a cold water-bath. After 3 h the mixture was filtered through hyflo and the filtrate evaporated. The residue was partitioned between water (20 ml), carefully basified with solid sodium carbonate, and EA (2×40 ml). The combined organic extracts were washed with saturated brine, dried and evaporated. The residue was chromatographed with 2 to 4% MeOH in DCM as eluent to give title compound (338 mg) as a yellow solid, m.p.194°.

T.l.c. (95:5 DCM-MeOH) Rf 0.15

INTERMEDIATE 15

N-methyl-2-nitroaniline

Methylamine hydrochloride (2.7 g) and a 10% aqueous solution of sodium hydroxyde (30 ml) were added to a solution of 1-fluoro-2-nitrobenzene (2.82 g) in THF (20 ml). The mixture was kept at 23° for 24 h. The reaction mixture was then concentrated in vacuo, taken up with 10% aqueous sodium hydroxide (30 ml) and extracted with EA (3×30 ml). The combined organic layers were washed with a saturated ammonium chloride solution (50 ml), brine (50 ml) and dried. Evaporation of the solvent gave the title compound as an orange oil (2.894 g).

T.l.c. EA/CH 1:4 Rf=0.57.

INTERMEDIATE 16

N-methyl-2-aminoaniline

10% palladium over charcoal (3.92 g) was added to a solution of intermediate 15 (2.8 g) in methanol (50 ml). The mixture was hydrogenated at atmospheric pressure for 9 h, then filtered on a celite pad and evaporated in vacuo to give the title compound as a brown oil (1.765 g). T.l.c. EA/CH 1:2 Rf=0.31:

INTERMEDIATE 17

Adamantane-1-carboxylic acid )2-methylamino-phenyl) amide

A solution of intermediate 16 (1.76 g) in EA (50 ml) and a solution of adamantylcarbonyl chloride (2.60 g) in EA (50 ml) were simultaneously added dropwise (during 1 h) to a solution of triethylamine (2 ml) in EA (150 ml). As soon as the addition was completed the mixture was evaporated under reduced pressure, diluted with DCM (200 ml) and washed with 10% aqueous sodium hydroxide (200 ml), with a saturated ammonium chloride solution (200 ml), and brine (200 ml). The organic layer was dried and concentrated in vacuo to give an off-white solid (3.62 g), which was purified by flash chromatography (eluting with CH/EA 7:1, 5:1 and 3:1) to give the title compound as pale brown solid (2.944 g). T.l.c. 0H/EA 4:1 Rf=0.39

INTERMEDIATE 18

N-adamantane-1-methyl-N'-methyl-benzene-1,2-diamine

To a solution of intermediate 17 (2.96 g) in dry toluene (60 ml) refrigerated at 0°, borane methyl sulfide complex (2.71 ml) was added dropwise under a nitrogen atmosphere.

14

The mixture was allowed to warm to 23° and then refluxed for 2.5 h. After cooling of the solution, an aqueous saturated solution of potassium carbonate (1 00 ml) was carefully added. The mixture was then diluted with EA (200 ml) and washed with saturated acqueous potassium carbonate (100 ml), brine (200 ml) and dried. The residue obtained after concentration in vacuo was taken up with methanol (60 ml) then solid sodium carbonate (11.02 g) was added and the suspension was refluxed for 17 h and kept at room temperature for 3 days. The mixture was evaporated, diluted with EA (200 ml) and washed with 5% acqueous ammonia (200 ml) and brine (200 ml). The organic layer was dried over sodium sulphate and concentrated in vacuo to an oil which was purified by flash-chromatography (eluting with CH/EA 19:1 ) to give the title compound as a brownish wax (0.698 g). T.l.c. CH/EA 19:1 Rf=0.37.

INTERMEDIATE 19

1-(Adamantane-1-methy)-2.4-dioxo-5-methyl-3-phenylhydrazono-2,3,4,5-tetrahydro-1H-1,5-benzodiazepine A solution of intermediate 18 (0.690 g) in EA (50 ml) was added dropwise to a solution of phenylhydrazonomalonyl dichloride (0.753 g) in EA (50 ml). The mixture was stirred at 23° for 45 min then was kept at 50° for 1 h. The mixture was washed with 10% aqueous sodium hydroxide (100 ml), brine (100 ml) and dried. After concentration under reduced pressure the title compound was obtained as a yellow foam (1.104 g). T.l.c. EA/CH 1:4 Rf=0.35.

INTERMEDIATE 20

1-(Adamantane-1-methyl)-3-amino-2,4-dioxo-5-methyl-2,3,4,5-tetrahydro-1H-1,5-benzodiazepine To a solution of intermediate 19 (1.1 g) in dry methanol (80 ml) 10% palladium on charcoal (1.06 g) and ammonium formate (1.577 g) were added. The mixture was refluxed for 10 min then filtered on a celite pad, evaporated in vacuo, taken up with diethyl ether (200 ml) and extracted with 10% aqueous hydrochloric acid (200 ml). The aqueous layer was neutralized with solid sodium bicarbonate and then extracted with EA (250 ml) which was washed with brine (200 ml) and dried. Concentration in vacuo and purification by flash chromatography (eluting with DCM/MeOH 9:1 ) of the residue gave the title compound as a brownish foam (0.718 g). T.l.c. DCM/MeOH 9:1, Rf 0.5. IR :3370–3117 (NH); 1693, 1666 (C=O) cm⁻¹

INTERMEDIATE 21

(S)-(+)-2-(4-toluenesulphonyloxy-phenylacetic acid methyl ester (S)-(+)-Methyl mandelate (2.0 g) and triethylamine (1.67 ml) were dissolved in dry dichloromethane (50 ml). The mixture was cooled to 0° then a solution of 4-toluenesulphonyl chloride (9.151 g) in dry DCM (100 ml) was slowly added dropwise under stirring mantaining the temperature between −5° and 5°. The solution was kept at this temperature for 7.5 h. After this time, the mixture was washed with 10% aqueous hydrochloric acid (100 ml) and brine (100 ml), dried and concentrated in vacuo. The crude material was purified by flash chromatography (eluting with CH/EA 5:1 then 2:1 ) to give the title compound as a white wax (2.302 g). T.l.c. (CH/EA 2:1) R𝒇=0.54, HPLC: (+)/(−) =99/1 e.e.=98%, M.p.=57°–58° C.,

INTERMEDIATE 22

[1-(Adamantane-1-methyl)-2,4-dioxo-5-(methyl)-2,3,4,5-tetrahydro-1H-1,5-benzodiazepin-3-yl] aminophenylacetic acid methyl ester (Diasteroisomer 1)

Diisopropylethylamine (0.315 ml) was added to a solution of intermediate 20 (0.640 g) and intermediate 21 (1.441 g) in dry THF (20 ml). The mixture was refluxed for 7.5 h then it was concentrated under reduced pressure and diluted with dichloromethane (60 ml), washed with a saturated aqueous ammonium chloride solution (35 ml), brine (35 ml) and dried. After concentration in vacuo the crude material was repeatedly purified by flash chromatography (eluting with EA/CH 1:3 then 1:2 and 2:3) to give the title compound (0.105 g) as a white foam.

T.l.c. (ENCH 2:3) $R_f$=0.36, d.e.=100% (by NMR), M.p. 105°–110° C., $[\alpha]_D$=−127.5°

INTERMEDIATE 23

(−)-1-)Adamantane-1-methyl)-3-amino-2,4-dioxo-5-methyl-2,3,4,5-tetrahydro-1H-1,5-benzodiazepine 20% Palladium (II) hydroxide on charcoal (0.130 g) was added to a solution of intermediate 22 (0.093 g) in methanol (10 ml). The mixture was hydrogenated at atmospheric pressure during 2 h. Then the mixture was filtered on a celite pad and evaporated under reduced pressure. The crude material was purified by flash chromatography (eluting with DCM/MeOH 19:1) to give the title compound as a colorless oil (0.058 g). T.l.c. (DCM/MeOH 9:1) $R_f$=0.70, 1H-NMR: 7.4–7.25 (m), 4.43 (d), 4.08 (s), 3.50 (s), 3.19 (d), 1.825 (bs), 1.52 (m), 1.21 (m).

INTERMEDIATE 24

N-(1-adamantane-1-methyl)-N'-(2-hydroxyethyl)-1,2-benzenediamine

2-Chloroethanol (8.36 ml) and powdered potassium hydroxide (7.0 g) were added to a solution of intermediate 1 (8.0 g) in DMSO (100 ml). The mixture was heated at 140° for 6 h, then it was diluted with water (200 ml) and extracted with diethyl ether (2×150 ml). The combined organic layers were washed with a saturated ammonium chloride solution (200 ml), brine (200 ml) and dried. Evaporation of the solvent gave a crude material which was purified by flash-chromatography (eluting with ENCH 1:9) to give the title compound as an off-white solid (4.6 g).

T.l.c. ENCH 7:10 $R_f$=0.58. M.p. 90°–95° C. IR: 3337 (NH+OH), 1601 (C=C) cm$^{-1}$

INTERMEDIATE 25

N-(Adamantane-1-methyl)-N'-[2-(dimethyltertbutylsilyloxy)ethyl]-1,2-benzenediamine Tertbutyldimethylsilyl chloride (2.8 g) and imidazole (2.5 g) were added to a solution of intermediate 24 (4.6 g) in dry DMF (100 ml). The mixture was stirred at 23° for 15 h, then it was diluted with diethyl ether (300 ml) and washed with a saturated ammonium chloride solution (200 ml), brine (300 ml) and dried. Evaporation under reduced pressure gave the title compound as a white solid (6.15 g,). T.l.c. EA/CH 4:11 Rf=0.9 M.p. 90°–95° C. $^1$H-NMR: 6.84–6.70 (m); 6.7–6.62 (m), 3.9 (t); 3.8–3.3 (bs), 3.17 (t), 2.75 (s), 2.00 (m); 1.8–1.4 (m); 0.91 (s), 0.09 (s),

INTERMEDIATE 26

1-(Adamantane-1-methyl)-2,4-dioxo-5-)2-hydroxyethyl]-3-phenylhydrazono-2,3,4,5-tetrahydro-1H-1,5-benzodiazepine A solution of intermediate 25 (6.15 g) in EA (150 ml) was added dropwise to a solution of phenylhydrazonomalonyl dichloride (4.4 g) in EA (100 ml). The mixture was refluxed for 3 h, then it was concentrated under reduced pressure and the residue was purified by flash-chromatography (eluting with EA/CH 1:9). The title compound was obtained as a yellow foam (4.0 g). T.l.c. ENCH 7:10 Rf=0.4. IR: 3437 (NH), 1641 (C-N) cm$^{-1}$.

INTERMEDIATE 27

1-(Adamantane-1-methyl)-3-amino-2,4-dioxo-5-(2-hydroxyethyl)-2,3,4,5-tetrahydro-1H-1,5-benzodiazepine 10% palladium on charcoal (1.06 g) and ammonium formate (2.53 g) were added to a solution of intermediate 26 (1.9 g) in dry methanol (80 ml). The mixture was refluxed for 1 h, then filtered on a celite pad, evaporated in vacuo, taken up with diethyl ether (100 ml) and extracted with 10% aqueous HCl (100 ml). The aqueous layer was neutralized with solid sodium bicarbonate and then extracted with DCM (200 ml) which was washed with bdne (100 ml) and dried. Concentration in vacuo gave the title compound as a white solid (1.21 g). T.l.c. EA/MeOH 4:1, Rf=0.38. M.p. 221°–223° C. IR :3144–3180 (NH+OH); 1691, 1659 (C=O) cm$^{-1}$

INTERMEDIATE 28

[1-(Adamantane-1-methyl)-2.4-dioxo-5-(2-hydroxyethyl)-2,3,4,5-tetrahydro-1H-1,5-benzodiazepin-3-yl]aminophenylacetic acid methyl ester (Diastereoisomer 1)

Diisopropylethylamine (0.366 ml) was added to a suspension of intermediate 27 (0.805 g) and intermediate 21 (1.34 g) in dry THF (50 ml). The mixture was refluxed for 8.5 h then it was concentrated under reduced pressure and diluted with dichloromethane (60 ml), washed with a saturated aqueous ammonium chloride solution (50 ml), brine (50 ml) and dried. After concentration in vacuo the crude material was repeatedly purified by flash chromatography (eluting with EA/CH 1:1 then 3:1) to give the title compound as a white foam (0.213 g). T.l.c. (EA/CH 3:2) $R_f$=0.40, d.e.=100% (by HPLC), M.p. 100°–107° C., $[\alpha]_D$=−125°,

INTERMEDIATE 29

(−)-1-(Adamantane-1-methyl)-3-amino-2,4-dioxo-5-(2-hydroxyethyl)-2,3,4,5-tetrahydro-1H-1,5-benzodiazepine 20% Palladium (II) hydroxide on charcoal (0.260 g) was added to a solution of intermediate 28 (0.195 g) in methanol (15 ml). The mixture was hydrogenated at atmospheric pressure during 2 h. Then the mixture was filtered on a celite pad and evaporated under reduced pressure. The crude material was purified by flash chromatography (eluting with EA/MeOH 3:1 ) to give the title compound as a white foam (0.125 g). T.l.c. (EA/MeOH 4:1) $R_f$=0.38, $[\alpha]_D$=−44.6°, M.p. 152°–157°.

INTERMEDIATE 30

1-(3-methyl-1-butyl)amino-2-nitrobenzene

A solution of 1-amino-3-methylbutane (1.5 g) in THF (20 ml) was dropped into a solution of 2-fluoronitrobenzene (2.4 g) in THF (20 ml), at 23° under a nitrogen atmosphere. The mixture was stirred at 23° for 3 h, then heated at reflux for 1.5 h. The mixture was allowed to cool to 23°, then concentrated under vacuum to give a crude compound which was purified by flash chromatography (eluting with CH-EA 9:1) to give the title compound as a yellow oil (2.12 g). T.l.c. CH-EA (4:1) Rf=0.79.

INTERMEDIATE 31

N-(3-methylbut-1-yl)-1,2-benzenediamine

A solution of potassium carbonate (9.1 g) and sodium hydrosulfite (8.0 g) in water (50 ml) was added to a mixture of intermediate 30 (2.12 g) in ethanol (30 ml) and water (70 ml). The mixture was stirred at 23° for 1 h, then acidified with concentrated hydrochloric acid until pH=3. The mixture was then basified with a 10% sodium hydroxide solution until pH=10 and extracted with ethyl acetate (2×100 ml); the combined extracts were washed with brine (150 ml), dried and concentrated in vacuo to give the title compound as a brown oil (1.8 g). T.l.c. CH-EA (4:1) Rf=0.36.

INTERMEDIATE 32

N-(2,2-dimethylethoxycarbonyl)-N'-(3-methyl-1-butyl)-1,2-benzenediamine

Di-t-butyl dicarbonate (2.44 g) and sodium hydrogen carbonate (1.42 g) were added to the solution of intermediate 31 (3.0 g) in THF (50 ml) and water (40 ml); the mixture was stirred at 30° for 1.5 h and concentrated in vacuo. The residue was diluted with ethyl acetate (150 ml) and washed with water (50 ml) and brine (50 ml). The organic layer was dried and concentrated in vacuo to an oil, which was purified by flash chromatography (eluting with CH/EA 9:1) to give the title compound as a wax (3.1 g). T.l.c, CH-EA (9:1), Rf=0.37.

INTERMEDIATE 33

2-Benzyloxycarbonylaminopropanedioic acid diethylester

To a solution of 2-aminomalonic acid diethyl ester (10.0 g) in dioxane (60 ml) and water (36 ml), potassium hydrogen carbonate (10.4 g) was added. After completion of the effervescence benzylchloroformate (7.4 ml) was added. The mixture was stirred at 23° for 1.5 h then it was concentrated under reduced pressure, taken up with diethyl ether (400 ml) and washed with 5% HCl (50 ml) and brine (50 ml). The organic layer was dried over sodium sulphate and concentrated in vacuo to give the title compound as a colorless oil (13.6 g). T.l.c. EA/CH 1:4 Rf=0.25.

INTERMEDIATE 34

2-Benzyloxycarbonylaminopropanedioic acid monoethylester

To a solution of intermediate 33 (13.56 g) in ethanol (100 ml), potassium hydroxide (2.46 g) and water (20 ml) were added. The mixture was stirred at 23° for 4 h then was concentrated under reduced pressure and it was coevaporated from absolute ethanol (40 ml). The residue was triturated with diethyl ether (80 ml) to give a white solid. After filtration the solid was suspended in diethyl ether (300 ml) and washed with 10% HCl (100 ml). The organic phase was washed with brine (60 ml) and dried over sodium sulphate. Evaporation gave the title compound as a white solid (9.4 g). M.p. 65°-70°.

INTERMEDIATE 35

N-(2,2-dimethylethoxycarbonyl)-N'-[2-)-1-benzyloxycarbonylamino-1-ethoxycarbonyl)-2-oxo ethyl]-N'-(3-methyl-1-butyl)1,2-phenylenediamine To a solution of intermediate 34 (0.90 g) in EA (40 ml), N,N'-dicyclohexycarbodiimide (0.76 g) and 1-hydroxybenzotriazole hydrate (0.55 g) were added. After complete addition the mixture was stirred at 20° for 1 h, then a solution of intermediate 32 (0.88 g) in EA (20 ml) was added and stirring was continued for 2 h. The reaction mixture was then heated at reflux for 4 h and left at 20° for 20 h, filtered, and washed with water (50 ml) and brine (50 ml). The organic layer was dried, concentrated in vacuo and the residue was purified by flash chromatography (eluting with CH/EA 9:1 ) to give the title compound as an oil (0.64 g). T.l.c. CH-EA (4:1), Rf=0.33.

INTERMEDIATE 36

1-(3-methyl-1-butyl)-3-benzyloxycarbonylamino-2,4-dioxo-2,3,4,5-tetrahydro-1H-1,5-benzodiazepine Concentrated hydrocloric acid (5 ml) was added to a suspension of intermediate 35 (0.64 g) in ethanol (15 ml). The mixture was stirred at 23° for 2 h, diluted with EA, washed with water, dried and concentrated in vacuo to an oil (0.49 g), which was purified by flash chromatography (eluting with EA-CH 1:1 ) to give the title compound as a white foam (0.23 g). T.l.c. EA-CH 1:1, Rf=0.59. IR :3431, 3256 (NH); 1734, 1717 (C=O) cm$^{-1}$

INTERMEDIATE 37

3-benzyloxycarbonylamino-5-butyl-2,4-dioxo-1-(3-methyl-1-butyl)-2,3,4,5-tetrahydro-1H-1,5-benzodiazepine An 80% suspension of sodium hydride in oil (0.016 g) was added to a solution of intermediate 36 (0.198 g) in dry DMF (5 ml). After 15 min the mixture was allowed to react with butyl bromide (0.135 ml). The solution was stirred at 23° for 1 h and then diluted with water (30 ml) and extracted with diethyl ether (3×30 ml). The combined organic layers were washed with brine (30 ml) and dried.

Concentration in vacuo gave the title compound as a colorless oil (0.226 g). T.l.c. EA-CH 1:2, Rf=0.47.

INTERMEDIATE 38

3-amino-5-butyl-2,4-dioxo-1-(3-methyl-1-butyl)-2,3,4,5-tetrahydro-5H-1,5-benzodiazepine 10% Pd/C (0.106 g) was added to a solution of intermediate 37 (0.220 g) in methanol (16 ml) and the mixture was hydrogenated at 1 atm. for 45 min. The catalyst was filtered over celite and the filtrate concentrated in vacuo to give the title compound as a yellow oil (0.181 g). T.l.c. EA-MeOH (4:1), Rf=0.53.

INTERMEDIATE 39

N-(2-Methoxy)ethyl-2-nitroaniline

Potassium carbonate (4.15 g) and 2-methoxyethylamine (1.3 ml) were added to a solution of 1-fluoro-2-nitrobenzene (1.56 ml) in dry THF (20 ml). The mixture was stirred at 23° for 24 h, then it was diluted with ethyl acetate, washed with a saturated ammonium chloride solution (100 ml), 10% sodium hydroxide solution (100 ml) and brine (100 ml), dried and concentrated in vacuo. The residue was purified by flash chromatography (eluting with CH-EA 3:1) to give the title compound as an orange oil (2.55 g). T.l.c. CH-EA (2:1), $R_f$ 0.51.

INTERMEDIATE 40

N-(2-Methoxy)ethyl-1,2-benzenediamine

A solution of potassium carbonate (12.5 g) and sodium hydrosulfite (15.6 g) in water (130 ml) was added dropwise to a solution of intermediate 39 (2.37 g) in ethanol (150 ml). The mixture was stirred at 23° for 24 h, then acidified with conc. hydrochloric acid until pH=3. The mixture was concentrated to half volume then basified with a 10% sodium hydroxide solution until pH=10. The residue was extracted with ethyl acetate (2×100 ml); the combined extracts were washed with brine (100 ml), dried and concentrated in vacuo to give the title compound as a dark brown oil (1.08 g). T.l.c. CH-EA (8:2), $R_f$=0.31.

INTERMEDIATE 41

N-(1-Adamantyl)methyl-N'-)2-methoxyethyl)-1,2-benzenediamine

Glacial acetic acid (0.38 ml) was added to a solution of intermediate 40 (1.08 g) and 1-adamantanecarboxaldehyde (1.01 g) in methanol (55 ml), then, sodiocyanoborohydride (0.76 g) was added portionwise. The mixture was stirred at 23° for 5 h, then concentrated in vacuo. The residue was taken up in ethyl acetate (200 ml) washed with a 5% sodium bicarbonate solution (150 ml), a saturated sodium bicarbonate solution (150 ml) and brine (100 ml), dried and concentrated in vacuo; the residue was purified by flash chromatography (eluting with CH-EA 6:4) to give the title compound as a dark oil (2.06 g). T.l.c. CH-EA (1:1 ), $R_f$=0.91.

INTERMEDIATE 42

1-(1-Adamantyl)methyl-2,4-dioxo-5-)2-methoxyethyl)-3-phenylhydrazono-2,3,4,5-tetrahydro-1H-1,5-benzodiazepine A solution of 2-phenylhydrazonomalonyldichloride (1.66 g) in dry THF (60 ml) was added dropwise to a solution of intermediate 41 in THF (60 ml). After complete addition the mixture was refluxed under a nitrogen atmosphere for 4 h. The solution was diluted with ethyl acetate, washed with a saturated sodium bicarbonate solution (3×150 ml) and brine (2×150 ml), dried and concentrated in vacuo. The residue was purified by flash chromatography (eluting with CH-EA 8:2) to give the title compound as a yellow foam (2.78 g). T.l.c. CH-EA (8:2), $R_f$=0.37. IR: 3441 (NH), 1663 (C=O) cm$^{-1}$.

INTERMEDIATE 43

1-H -Adamantyl)methyl-3-amino-2.4-dioxo-5-(2-methoxyethyl)-2,3,4,5-tetrahydro-1H-1.5-benzodiazepine Ammonium formate (3.20 g) and 10% palladium on charcoal (1.23 g) were added to a solution of intermediate 42 (2.42 g) in dry methanol (80 ml). The mixture was refluxed for 1 h, under a nitrogen atmosphere, then cooled to 23° and filtered over celite. The filtrate was concentrated in vacuo; the residue was taken up in ethyl acetate (100 ml), extracted with a 10% hydrochloric acid solution (100 ml) and brine (100 ml). The aqueous layer was neutralized with solid sodium bicarbonate, then extracted with methylene chloride (4×100 ml). The organic layer was washed with brine (100 ml), dried and concentrated in vacuo to a residue, which was purified by flash chromatography (eluting with DCM-MeOH 94:4) to give the title compound as a white foam (1.04 g). T.l.c. EA-MeOH (95:5), $R_f$=0.34. IR: 3373 and 3317 (NH), 1697 and 1666 (C=O) cm$^{-1}$.

INTERMEDIATE 44

N-(1-adamantane-1-methyl)-N'-(3-hydroxypropyl)-1,2-benzenediamine

2-Bromopropanol (0.7 ml) and powdered potassium hydroxide (0.312 g) were added to a solution of intermediate 1 (1.0 g) in DMF (10 ml). The mixture was heated at 140° for 1 h and 30 min., then it was diluted with water (100 ml) and extracted with diethyl ether (2×70 ml). The combined organic layers were washed with brine (100 ml) and dried. Evaporation of the solvent gave a crude material which was purified by flash-chromatography (eluting with ENCH from 1:3 to 1:1 ) to give the title compound as a red-brown oil (0.430 g). T.l.c. ENCH 1:1 Rf=0.60.

INTERMEDIATE 45

1-(Adamantane-1-methy)-2,4-dioxo-5-)3-hydroxypropyl)-3-phenylhydrazono-2,3,4,5-tetrahydro-1H-1,5-benzodiazepine A solution of intermediate 44 (0.430 g) in EA (10 ml) and a solution of phenylhydrazonomalonyl dichloride (0.365 g) in EA (10 ml) were dropped into a flask containing ethyl acetate (10 ml). The mixture was stirred at 23° for 40 min, then at 500 for 30 min, then it was cooled to 23° C., washed with water (20 ml), 10% sodium hydroxide solution (2×20 ml) and brine (20 ml), dried and concentrated in vacuo. The residue was purified by flash-chromatography (eluting with EA:CH from 1:1 to 1:0) to give the title compound as a yellow foam (0.270 g). T.l.c. EA:CH 1:1 Rf=0.39.

INTERMEDIATE 46

1-(Adamantane-1-methyl)-3-amino-2,4-dioxo-5-(3-hydroxypropyl)-2,3,4,5-tetrahydro-1H-1.5-benzodiazepine 10% palladium on charcoal (0.850 g) and ammonium formate (1.20 g) were added to a solution of intermediate 45 (0.930 g) in dry methanol (70 ml). The mixture was refluxed for 40 min., then filtered on a celite pad and evaporated in vacuo. The residue was taken up with dichloromethane (100 ml), washed with water (35 ml), 2% sodium hydroxide solution (35 ml) and brine (35 ml), dried, and concentrated in vacuo to give the title compound as a white wax (0.665 g). T.l.c. EA:MeOH 9:1, Rf=0.15. IR:3194 (NH+OH); 1688, 1680 (C=O) cm$^{-1}$

INTERMEDIATE 47

N-[1-(Adamantane-1-methyl)-2,4-dioxo-5-(3-hydroxypropyl)-2,3,4,5,tetrahydro-1H-1,5-benzodiazepine-3yl]-2-D-(3-tertbutoxycarbonyl)-3-phenylpropionamide N,N'-dicyclohexylcarbodiimide (0.179 g) and 1-hydroxybenzotriazole (0.117 g) were added to a solution of N-(tert-butoxycarbonyl)-D-phenylalanine (0.207 g) in ethyl acetate (20 ml). The solution was stirred at 23° for 1 h, then a solution of intermediate 46 (0.300 g) in ethyl acetate (10 ml) was added. The resulting solution was stirred at 23° for 2 h and 30 min., then it was diluted with ethyl acetate (50 ml), washed with water (20 ml) and brine (20 ml), dried and concentrated in vacuo. The residue was purified by flash chromatography using a gradient of EA-CH (1:1 to pure EA) as eluant to afford the title compound as a white foam (0.230 g). T.l.c. EA-CH (3:1) Rf=0.5.

INTERMEDIATE 48

N-[1-)Adamantane-1-methyl)-2,4-dioxo-5-(3-hydroxypropyl)-2,3,4,5,tetrahydro-1H-1,5-benzodiazepine-3-yl]-2-D-amino-3-phenylpropionamide (Diastereoisomer 1 and Diastereoisomer 2)

Intermediate47 (0.730 g) was dissolved in a mixture of trifluoroacetic acid (15 ml) and dicloromethane (15 ml) and stirred at 23° for 30 min. The reaction mixture was concentrated in vacuo and triturated with diethyl ether to give the trifluoroacetic salt of the title compound. This salt was suspended in ethyl acetate (70 ml) and extracted with a 5% ammonia solution (70 ml). The organic layer was washed with brine, dried and concentrated in vacuo to give a white foam (0.540 g). Separation of the two diastereomers was achieved by flash chromatography eluting with a gradient of EA-MeOH (97:3 to 9:1) to give the title compounds, diastereomer 1, (0.233 g), and diastereomer 2 (0.188 g), as white foams. T.l.c. EA-MeOH (9:1) R$_f$=0.45 and 0.33. I.R :3381 and 3182 (NH+NH$_2$); 1699 and 1680 (C=O) cm$^{-1}$.

Diastereoisomer 1: $^1$H-NMR: 8.53 (d); 8.52–7.2 (m); 5.09 (d); 4.42 (d); 4.25 (m); 3.84 (m); 3.76 (m); 3.68 (dd); 3.30 (dd); 3.25 (d); 2.64 (dd); 2.8–2.65 (m); 2.25–2.02 (m); 1.84 (bs); 1.65–1.4 (m); 1,25 (m).

INTERMEDIATE 49

N-[1-(Adamantane-1-methyl)-2,4-dioxo-5-(3-hydroxypropyl)-2,3,4,5-tetrahydro-1H-1,5-benzodiazepin-3-yl]-3-phenyl-2-D-(3-phenylthioureido)-propionamide Phenylisothiocyanate (0.054 ml) was added to a solution of intermediate 48 Diastereoiosmer 1 (0.233 g) in dichloromethane (10 ml). The solution was stirred at 23° for 3 h and at 50° for 30 min. The solvent was evaporated in vacuo and the residue was purified by flash chromatography using EA-CH (from 1:1 to 3:1) as eluant to afford the title compound as a white foam (0.185 g) T.l.c. EA-CH (3:1) Rf=0.48.

INTERMEDIATE 50

1-(Adamantane-1-methyl)-3-amino-2,4-dioxo-5-)3-hydroxypropyl)-2,3,4,5-tetrahydro-1H-1,5-benzodiazepine Intermediate 49 (0.170 g) was dissolved in trifluoroacetic acid (5 ml) and the mixture was stirred at 42° C. for 40 h. The solution was concentrated in vacuo and the residue was purified by flash chromatography, to give only recovered starting material (0.120 g). This material was redissolved in a 1:1 mixture (6 ml) of conc. hydrochloric acid and ethanol and stirred at 80° C. for 20 h. The solution was concentrated in vacuo, the residue was diluted with ethyl acetate (20 ml) and washed with a 5% ammonia solution (20 ml) and brine. The organic phase was dried and concentrated in vacuo; the residue was purified by flash chomatography using EA-MeOH (9:1) as eluants to afford the title compound (0.020 g), which was not further characterized and was used without further purification in Example 14. T.l.c. EA:MeOH 9:1, Rf=0.15.

EXAMPLE 1

N-[1-(1-Adamantylmethyl)-2,4-dioxo-5-(3-methylbut-1-yl)-2,3,4,5-tetrahydro-1H-1,5-benzodiazepin-3-yl]-N'-phenylurea Phenyl isocyanate (0.022 ml) was added to a solution of the intermediate 4 (0.07 g) in dry dichloromethane (10 ml) under a nitrogen atmosphere. The mixture was stirred at 23° for 1 h, then concentrated in vacuo to a residue which was triturated with acetonitrile to give the title compound as a white solid (0.066 g). M.p. 156°–7°. T.l.c. CH-EA(1:1), Rf 0.53. IR :3325 (NH), 1701,1688 and 1645 (C=O), 1553 (C=C) cm–1;

EXAMPLE 2

N-[1-(1-Adamantylmethyl)-2,4-dioxo-5-(3-methylbut-1-yl)-2,3,4,5-tetrahydro-1H-1,5-benzodiazepin-3-yl]-N'-[3-(N,N-dimethylamino)phenyl]urea 3-(N,N-Dimethylamino)phenyl isocyanate (0.033 g) was added to a solution of the intermediate 4 (0.07 g) in dry dichloromethane (5 ml) under a nitrogen atmosphere. The mixture was stirred at 23° for 1 h, then concentrated in vacuo to a residue which was triturated with acetonitrile to give the title compound as a white solid (0.045 g). M.p. 226°–7°. T.l.c. CH-EA(1:1), Rf 0.53. IR :3400 and 3306 (NH), 1700 and 1699 (C=O), 1628 and 1587 (C=C) cm$^{-1}$; $^1$H-NMR :7.43–7.27 (m); 7.15 (t); 6.78 (t); 6.60 (m);6.46 (m);6.37 (m); 6.19 (d); 5.07 (d); 4.38 (d); 3.90 (m); 3.23 (d); 2.92 (s); 1.82 (m); 1.80–1.1 (m); 0.93 (d).

EXAMPLE 3

N-[1-(1-Adamantylmethyl)-2,4-dioxo-5-)cyclohexyl)-2,3,4,5-tetrahydro-1H-1,5-benzodiazepin-3-yl]-N'-phenylurea Phenyl isocyanate (0.06 ml) was added to a solution of the intermediate 9 (0.192 g) in dry dichloromethane (5 ml) and acetonitrile (5 ml) under a nitrogen atmosphere. The mixture was stirred at 23° for 1 h, then the obtained white precipitate was filtered and dried under vacuum to give the title compound as a white solid (0.182 g). M.p. 218°–9°. T.l.c. CH-EA(8/2), Rf 0.14. IR :3306 (NH), 1697,1664 and 1637 (C=O), 1601,1560 (C=C) cm-1;

EXAMPLE 4

1-(1-Adamantylmethyl)-3-[3-(N,N-dimethylamino)phenyloxycarbonyl]amino-2, 4-dioxo-5-(3-methylbut-1-yl)-2,3,4,5-tetrahydro-1H-1,5-benzodiazepine Pyridine (0.027 ml) and 3-(N,N-dimethylamino)phenyl chloroformate (0.068 g) were added to a solution of the intermediate 4 (0.07 g) in dry dichloromethane (10 ml) under a nitrogen atmosphere. The mixture was stirred at 23° for 30 min, then washed with 5% hydrochloric acid, 5% sodium hydrogen carbonate (20 ml) and brine (20 ml). The organic layer was dried and concentrated in vacuo to a solid which was triturated with diethyl ether to give the title compound as a beige solid (0.045 g). M.p. 172°–3°. T.l.c. CH-EA(1:1), Rf 0.69. IR :3447 and 3315 (NH), 1734,1695 and 1674 (C=O), 1616 (C=C) cm-1;

EXAMPLE 5

1-(1-Adamantan-1-yl-5-methyl-2,4-dioxo-2,3,4,5-tetrahydro-1H-benzo[b][1,4]diazepine-3-yl)-3-m-tolyl-urea m-Tolylisocyante (33 mg) was added to a suspension of intermediate 14 (76 mg) in dry MeCN (1 ml) at 23° under nitrogen. After 50 min the thick slurry was suspended in diethyl ether and the solid filtered off and dried at 50° in vacuo to give the title compound (78 mg) as a white solid, m.p. 245°–7°.

T.l.c. (95:5DCM-MeOH) Rf 0.43

I.R. (KBr disc) 3318;2907;1701;1671;1558;1497;1388;1229;763cm$^{-1}$.

The title compound was separated into its two enantiomers by chiral HPLC.

Column: Chiralcel OJ; 25cm×20 mm id

Eluent: Heptane-EtOH (90:10)

Flow-rate: 20 ml min$^{-1}$

Detection: uv @254nm

Isomer 1 (14 mg) was obtained as a white solid, m.p. 212°–3°

T.l.c. (95:5 DCM-MeOH) Rf 0.43

H.p.l.c..99%ee

M.s. MH* obs =473 amu.

Isomer 2 (17 mg) was obtained as a white solid, m.p. 213°–5°

T.l.c. (95:5 DCM-MeOH) Rf 0.43

H.p.l.c. >99% ee
M.s. MH⁺obs =473amu.

EXAMPLE 6

1-(1-Adamantan-1-yl-5-methyl-2,4-dioxo-2,3,4,5-tetrahydro-1H-benzo[b][1.4]diazepine-3-yl)-3(4-fluorophenyl)-urea 4-Fluorophenylisocyante (36 mg) was added to a suspension of intermediate 14 (79 mg) in dry acetonitrile (1 ml) at 23° under nitrogen. Aftern 50 min the thick slurry was suspended in DE and the solid filtered off and dried at 50° in vacuo to give the title compound 73 mg) as a white solid, m.p. 239°–41°.

T.l.c. (95:5 DCM-MeOH) Rf 0.43
I.r. (KBr disc) 3334;2908;1700;1557;1510;1391;1214cm⁻¹

EXAMPLE 7

3-[3-(1-Adamantan-1-yl-5-methyl-2,4-dioxo-2,3,4,5-tetrahydro-1H-benzo[b][1,4]diazepine-3-yl)-ureido]benzoic acid (a) A solution of 3-amino-benzoic acid, benzyl ester in dry THF (2 ml) was cooled to 0° under nitrogen and treated with Et₃N (73 mg) then triphosgene (69 mg). The fawn slurry was treated with more Et₃N (73 mg) then stirred at 0° for 30 min. A solution of intermediate 14 (179 mg) in dry THF (2 ml) was added and stirring continued at 23° for 3.5 h whereupon the mixture was poured into phosphate buffer solution (pH6.5;30 ml) and extracted with DCM (2×30 ml). The combined, dried extracts were evaporated and the residue chromatographed with 1% MeOH in DCM as eluent to give a beige foam (210 mg) m.p. 126°–8°. A portion of this foam (193 mg) was dissolved in tetrahydrofuran (15 ml) and hydrogenated at 23° and 1 atm pressure in the presence of 10% palladium on carbon as catalyst (35 mg). After 40 min the mixture was filtered through a glass microfibre filter (1.6 μm) and the filtrate evaporated to give the title compound (147 mg) as a white solid, m.p. 198° dec.

T.l.c. (90:10 DCM-MeOH) Rf 0.43
I.r. (KBr disc) 3377;2908;1695;1556;1497;1393;1228;761 cm⁻¹.

EXAMPLE 8

(−)-N-[1-(Adamantylmethyl)-2,4-dioxo-5-methyl-2,3,4,5-tetrahydro-1H-1,5-benzodiazepin-3-yl]-N'-phenylurea Phenyl isocyanate (0.032 ml) was added to a solution of intermediate 23 (0.050 g) in dry acetonitrile (1 ml). The mixture was allowed to stand at 23° for 5 min, then it was evaporated under reduced pressure. The crude material obtained was purified by flash chromatography (eluting with ENCH 1:2) to give the title compound as a white solid (0.49 g). T.l.c. (ENCH 2:3) R$_f$=0.39, HPLC: e.e.=92%, [α]$_D$=−75.1°, M.p.: 173°–178° C. ¹H-NMR: 7.44–7.24 (m), 7.05 (t), 6.98 (bs), 6.17 (d), 5.14 (d), 4.40 (d), 3.50 (s), 3.18 (d), 1.82 (m), 1.60–1.14 (m). IR(nujol): 3300–3200 (NH), 1703, 1659 (C=O), 1599 (C=C).

EXAMPLE 9

N-[1-(Adamantylmethyl)-2,4-dioxo-5-(2-hydroxyethyl)-2,3,4,5-tetrahydro-1H-1,5-benzodiazepin-3-yl]-N'-phenylurea Phenyl isocyanate (0.013 ml) was added to a solution of intermediate 27 (0.030 g) in dry DCM (3 ml). The solid obtained after evaporation in vacuo was purified by flash chromatography (eluting with EA-CH 1:2 then 2:1). The title compound was obtained as a white solid (0.039 g). M.p. 177°–180° T.l.c. EA/CH 2:1, Rf 0.58. IR: 3352 (NH+OH), 1695, 1653 (C=O) cm⁻¹; ¹H-NMR: 7.802 (dd); 7.32 (dd); 7.38–7.20 (m); 7.135 (bs); 7.014 (tt); 6.435 (d); 5.12 (d); 4.393 (d); 4.3–4.18 (m); 3.907 (bd); 3.781 (m); 3.56 (bs); 3.415 (d); 1.824 (s); 1.523 (m); 1.231 (m).

EXAMPLE 10

N-[1-(Adamantylmethyl)-2,4-dioxo-5-)2-hydroxyethyl)-2,3,4,5-tetrahydro-1H-1,5-benzodiazepin-3-yl]-N'-(3-methylphenyl)urea 3-Tolyl isocyanate (0.037 ml) was added to a solution of intermediate 27 (0.100 g) in dry DCM (12 ml). The solid obtained after evaporation in vacuo was purified by flash chromatography (eluting with EA-CH 2:1). The title compound was obtained as a pale orange solid (0.125 g). M.p. 155°–160° T.l.c. EA/CH 1:1, Rf 0.39. IR: 3300, 3150 (NH+OH), 1713, 1688 (C=O), 1612, 1597 (C=C) cm⁻¹; ¹H-NMR: 7.78 (d); 7.40–7.06 (m); 6.86 (d); 6.80 (bs); 6.28 (d); 5.11 (d); 4.40 (d); 4.23 (m); 3.91 (m); 3.80 (m); 3.39 (bs); 3.22 (d); 2.20 (s); 1.82 (m); 1.6–1.2 (m).

EXAMPLE 11

(−)-N-[1-(Adamantylmethyl)-2,4-dioxo-5-(2-hydroxyethyl)-2,3,4,5-tetrahydro-1H-1,5-benzodiazepin-3-yl]-N'-phenylurea Phenyl isocyanate (0.051 ml) was added to a solution of intermediate 29 (0.120 g) in dry DCM (5 ml). The mixture was allowed to stand at 23° for 5 min, then it was evaporated under reduced pressure. The crude material obtained was purified by flash chromatography (eluting with EA/CH 1:2 then 2:1) to give the title compound as a white solid (0.133 g). T.l.c. (EA/CH 2:1) R$_f$=0.58, HPLC: e.e.=93.2%, [α]$_D$=−50.2°, M.p.: 165°–170°.

EXAMPLE 12

N-[5-butyl-2,4-dioxo-1-(3-methylbut-1-yl)-2,3,4,5-tetrahydro-1H-1,5-benzodiazepin-3-yl]-N'-)4-methoxyphenyl)urea 4-methoxyphenyl isocyanate (0.070 ml) was added to a solution of the intermediate 38 (0.085 g) in dry DCM (5 ml). The reaction mixture was stirred at 23° for 5 min, then the mixture was directly put on the top of a column and purified by flash chromatography (eluting with ENCH 1:2 then 1:1 ) to give the title compound as a white solid (0.054 g). M.p. 245°–248° C. T.l.c. ENCH 1:1, Rf=0.40. IR: 1697, 1664 (C=O) cm⁻¹;

EXAMPLE 13

N-[1-(1-Adamantyl)methyl-2,4-dioxo-5-(2-methoxyethyl)-2,3,4,5-tetrahydro-1H-benzodiazepin-3-yl]-N'-phenylurea Phenyl isocyanate (0.015 ml) was added to a solution of intermediate 43 (0.054 g) in acetonitrile (10 ml). The reaction mixture was stirred at 23° C. for 30 min, then filtered. The solid was washed with acetonitrile and dried to give the title compound as a white solid (0.0485 g). M.p. 222°–4°. T.l.c. CH-EA 7:3, R$_f$=0.39. IR: 3325 and 3288 (NH), 1647 (C=O), 1595 (C=C) cm⁻¹;

The compound of Example 13 (0.107 g) was separated into its enantiomers via preparative chiral HPLC, using a Pirkle D-DNBPG C5 column (25cm×2cm id), flow rate 20 ml/min., at 254nm (UV detector), and eluting with DCM- IPA 93:7 v/v to give the enantiomer 1 (0.036 g) HPLC: retention time 4.00 min., enantiomeric excess 99.8%. IR (CDCl$_3$): 1691–1664 (CO) cm$^{-1}$.

Enantiomer 2 (0.41 g) HPLC: retention time 5.50 min., enantiomeric excess 95.6%. IR (CDCl$_3$): 1695–1686 (CO) cm$^{-1}$.

EXAMPLE 14

N-[1-(Adamantane-1-methyl)-2,4-dioxo-5-(3-hydroxypropyl)-2,3,4,5-tetrahydro-1H-1,5-benzodiazepin-3-yl]-N'-phenylurea Phenyl isocyanate (0.005 ml) was added to a solution of intermediate 50 (0.020 g) in acetonitrile (3 ml). The solid obtained was filtered, washed with diethyl ether and acetonitrile, triturated with acetonitrile, and dried to give the title compound as a white solid (0.024 g). Its enantiomeric purity was established by chiral HPLC and was found to be 98%. M.p. 186°–8° C. T.l.c. EA:MeOH 8:2, Rf 0.33. IR: 3500–3310 (NH+OH), 1695, 1641 (C=O); 1601 (C=C) cm$^{-1}$;

Pharmacy Example

| Capsules or Tablets | |
|---|---|
| | mg/dosage form |
| Active ingredient | 0.1 |
| Polyethyleneglycol | 15.0 |
| Lactose | 52.4 |
| Starch | 30.0 |
| Magnesium stearate | 0.5 |
| Silicon dioxide | 1.0 |
| Sodium Lauryl Sulphate | 1.0 |
| | 100.0 |

The active ingredient is dispersed in a suitable solvent (e.g. ethanol) together with polyethyleneglycol. The solvent is removed. The powder so obtained is blended with the other excipients. The blend can be used to fill gelatine capsules or compressed using appropriate punches. The tablets can be coated using conventional techniques and coatings.

| | |
|---|---|
| Active ingredient | 0.1 |
| Povidone | 15.4 |
| Lactose | 74.0 |
| Hydrogenated vegetable oils | 3.0 |
| Silicon dioxide | 1.0 |
| Sodium Laauryl sulphate | 1.5 |
| Crospovidone | 5.0 |
| | 100.0 |

The active ingredient is dispersed in a suitable solvent (e.g. ethanol) together with povidone. The solution is sprayed on to lactose and the solvent removed. The powder obtained is blended with the other excipients. The blend is used to fill gelatine capsules or comprssed using appropriate punches. The tablet can be coated using conventional techniques and coatings.

| Oral liquid | |
|---|---|
| Active ingredient | 70–100 microgramms/dose |
| ethanol | 5–15% |

| | |
|---|---|
| Sodium saccharinate | 0.1–1% |
| Propylene glycol | q.b. 100% |
| Injection Formulation | |
| Active ingredient | 0.1–100 microgramms |
| Sodium phosphate | 1.50 mg/ml |
| NaOH | qs desired pH (range 3–9) |
| glyerol | 10–500 mg/ml |
| water for injection | qs to 0.5–10 ml |

Pack in glass (ampules) with a rubber stopper (vials, syringes) and a plastic/metal overseal (vials only). An inert gas atmosphere (for example nitrogen) may be introduced into dead space of container.

CCK—Receptor Binding

The binding affinity of the compounds of the invention for the CCK-A receptor (Pancreas Assay) and CCK-B receptor (guinea pig cortex assay) was determined using the procedure of G Dal Forno et al J. Pharmacol. Exp & Ther. 261-1056–1063. The pKi values determined with respresentative compounds of invention were as follows:

| | pKi | |
|---|---|---|
| Compound Ex No | CCK-A | CCK-B |
| 1 | 6.54 | 8.86 |
| 2 | 6.02 | 8.25 |
| 3 | 6.25 | 8.62 |
| 4 | 5.80 | 8.12 |
| 8 | 6.4 | 9.0 |
| 9 | 6.49 | 8.85 |
| 10 | 6.8 | 9.4 |
| 11 | 6.14 | 9.6 |
| 12 | 6.16 | 8.69 |
| 14 | 6.09 | 9.41 |

The compounds of the invention are essentially non-toxic and therapeutically useful doses.

We claim:

1. A compound of general formula (I)

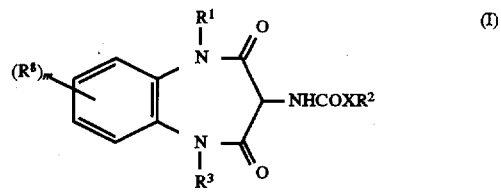

wherein

R$^1$ represents a C$_{3-7}$cycloalkyl, C$_{7-11}$ bridgedcycloalkyl or C$_{1-6}$alkyl group which alkyl group may be substituted by a hydroxy, C$_{1-4}$alkoxy, phenyl, C$_{1-6}$alkoxycarbonyl, C$_{3-7}$cycloalkyl, or C$_{7-11}$ bridgedcycloalkyl group;

R$^2$ represents a substituted or unsubstituted phenyl group (wherein the substituents may be 1 or 2 of halo, C$_{1-4}$alkyl, nitro, cyano, trifluoromethyl, trifluoromethoxy, C$_{1-4}$alkylthio or (CH$_2$)$_n$R$^4$ wherein R$^4$ is hydroxy, C$_{1-4}$alkoxy, CO$_2$R$^5$, NR$^5$R$^6$, SO$_2$NR$^5$COR$^7$, CONR$^5$SO$_2$R$^7$, or R$^4$ represents a tetrazole, carboxamidotetrazole or 3-trifluoromethyl-1,2-4-triazole group, which groups may be substituted on one of the nitrogen atoms by a C$_{1-4}$alkyl group; R$^3$ represents C$_{3-7}$cycloalkyl, C$_{7-11}$ bridged cycloalkyl or C$_{1-6}$alkyl which alkyl group may be substituted by a phenyl, C$_{3-7}$cycloalkyl or C$_{7-11}$ bridged cycloalkyl group;

$R^5$ represents hydrogen or a $C_{1-4}$alkyl group; $R^6$ independently represents hydrogen or a $C_{1-4}$alkyl group or the group $SO_2CF_3$;

$R^7$ represents $C_{1-4}$alkyl;

$R^8$ represents hydrogen or a halogen atom; m is zero, 1 or 2;

X represents oxygen or NH;

n is zero or 1; and pharmaceutically acceptable salts thereof.

2. A compound as claimed in claim 1 wherein X represents the group NH.

3. A compound as claimed in claim 1 wherein $R^8$ represents hydrogen.

4. A compound as claimed in claim 1 wherein the groups $R^5$ and $R^3$ are different.

5. A compound as claimed in claim 1 wherein $R^1$ represents methyl, propyl, isopropyl, butyl, 3-methylbutyl, 3,3-dimethyl butyl, 2-hydroxyethyl, 3-hydroxypropyl, methoxyethyl, ethoxycarbonylethyl, cyclohexyl or 1-adamantylmethyl.

6. A compound as claimed in claim 1 wherein $R^2$ is phenyl optionally substituted by methyl, methoxy, dimethylamino, fluoro or carboxy.

7. A compounds as claimed in claims 1 wherein $R^3$ represents 1-adamantyl, 1-adamantylmethyl, cyclohexylmethyl or 3-methylbutyl.

8. A compound as claimed in claim 1 wherein $R^1$ represents methyl, 3-methylbutyl, 2-hydroxyethyl, 3-hydroxypropyl, 2-ethoxycarbonylethyl, 2-methoxyethyl or cyclohexyl and $R^3$ represents 1-adamantylmethyl.

9. A compound as claimed in claim 1 wherein $R^1$ represents methyl and $R^3$ represents 1-adamantyl.

10. A compound selected from

N-[1-(Adamantylmethyl)-2,4-dioxo-5-(2-hydroxyethyl)-2,3,4,5-tetrahydro-1H-1,5-benzodiazepin-3-yl]-N'-phenylurea;

N-[1-(1-Adamantylmethyl)-2,4-dioxo-5-(2-methoxyethyl)-2,3,4,5-tetrahydro-1H-benzodiazepin-3-yl]-N'-phenylurea;

N-[1-(1-Adamantylmethyl)-2,4-dioxo-5-(3-methylbut-1-yl)-2,3,4,5-tetrahydro-1H-1,5-benzodiazepine-3-yl]-N'-phenylurea;

N-[1-(1-Adamantylmethyl)-2,4-dioxo-5-(cyclohexyl)-2,3,4,5-tetrahydro-1H-1,5-benzodiazepine-3-yl]-N'-phenylurea;

N-[1-Adamantylmethyl)-2,4-dioxo-5-(3-methylbut-1-yl)-2,3,4,5-tetrahydro-1H-1,5-benzodiazepine-3-yl]-N'-[3-(N,N-dimethylamino)phenylurea;

N-[1-Adamantylmethyl)-3-[3(N,N-dimethylamino) phenyloxycarbonyl]amino-2,4-dioxo-5-(3-methylbut-1-yl)-2,3,4,5-tetrahydro-1H-1,5-benzodiazepine;

N-[1-(Adamantylmethyl)-2,4-dioxo-5-(3-hydroxypropyl)-2,3,4,5-tetrahydro-1H-1,5-benzodiazepin-3-yl]-N'-phenylurea;

N-[1-(Adamantylmethyl)-2,4-dioxo-5-(2-ethoxycarbonylethyl)-2,3,4,5-tetrahydro-1H-1,5-benzodiazepin-3-yl]-N'-phenylurea, and enantiomers thereof.

11. A compound selected from 1-(1-Adamantan-1-yl-5-methyl-2,4-dioxo-2,3,4,5-tetrahydro-1H-benzo[b][1,4]diazepine-3-yl)-3-m-tolyl-urea;

1-(1-Adamantan-1-yl-5-methyl-2,4-dioxo-2,3,4,5-tetrahydro-1H-benzo[b][1,4]diazepine-3-yl)-3(4-fluoro-phenyl)-urea;

3-[3-(1-Adamantan-1-yl-5-methyl-2,4-dioxo-2,3,4,5-tetrahydro-1H-benzo[b][1,4]diazepine-3-yl)-ureido] benzoic acid; and more especially enantiomers thereof.

12. A pharmaceutical composition for the treatment of conditions where modification of the effects of gastrin and/or CCK is of therapeutic benefit comprising an effective amount of a compound as defined in claim 1 in admixture with one or more physiologically acceptable carriers or excipients.

13. A method of treatment of a mammal including man for conditions where modification of the effects of gastrin and or CCK is of therapeutic benefit comprising administration of an effective amount of a compound as defined in claim 1.

14. A process for the preparation of a compound of formula (I) which comprises (a) reacting an amine of formula (II) wherein $R^1, R^3, R^8$ and m are as defined in formula (I)

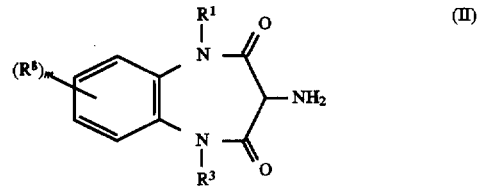

with an isocyanate $R^2NCO$ and compound of $R^2XCOCl$ wherein $R^2$ and X have the meanings defined in formula (I);

(b) reacting a compound corresponding to formula (I) but wherein $R^1$ or $R^3$ represents a hydrogen atom with an alkylating agent $R^1Y$ or $R^3Y$ wherein Y is a leaving group and $R^1$ or $R^3$ is an optionally substituted alkyl group as defined in formula (I) and thereafter if necessary or desired either before or alter any separation into its stereochemical isomers the conversion of one compound of the invention into another compound of the invention.

15. A compound of the formula (I)

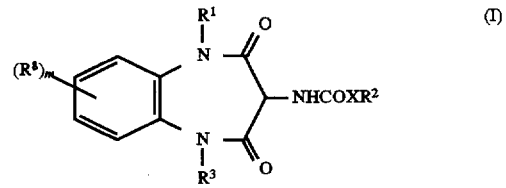

wherein $R^1$ represents a $C_{3-7}$cycloalkyl, $C_{7-11}$ bridgedcycloalkyl or $C_{1-6}$alkyl group which alkyl group may be substituted by a hydroxy, phenyl, $C_{1-6}$alkoxycarbonyl, $C_{3-7}$cycloalkyl, or $C_{7-11}$ bridgedcycloalkyl group;

$R^2$ represents a substituted or unsubstituted phenyl group (wherein the substituents may be 1 or 2 of halo, $C_{1-4}$alkyl, nitro, cyano, trifluoromethyl, trifluoromethoxy, $C_{1-4}$alkylthio or $(CH_2)_n R^4$ wherein $R^4$ is hydroxy, $C_{1-4}$alkoxy, $CO_2R^5$, $NR^5R^6$, $SO_2NR^5COR^7$, $CONR^5SO_2R^7$, or $R^4$ represents a tetrazole, carboxamidotetrazole or 3-trifluoromethyl-1,2-4-triazole group, which groups may be substituted on one of the nitrogen atoms by a $C_{1-4}$alkyl group; $R^3$ represents $C_{3-7}$cycloalkyl, $C_{7-11}$ bridged cycloalkyl or $C_{1-6}$alkyl which alkyl group may be substituted by a phenyl, $C_{3-7}$cycloalkyl or $C_{7-11}$ bridged cycloalkyl group;

$R^5$ represents hydrogen or a $C_{1-4}$alkyl group;

$R^6$ independently represents hydrogen or a $C_{1-4}$alkyl group or the group $SO_2CF_3$;

$R^7$ represents $C_{1-4}$alkyl;

$R^8$ represents hydrogen or a halogen atom; m is zero, 1 or 2;

X represents oxygen or NH;

n is zero or 1; and pharmaceutically acceptable salts thereof.

* * * * *